United States Patent
Ueno et al.

(10) Patent No.: US 7,981,662 B2
(45) Date of Patent: Jul. 19, 2011

(54) ANALYZER

(75) Inventors: Kunio Ueno, Kakogawa (JP); Seiichiro Tabata, Sanda (JP)

(73) Assignee: Sysmex Corporation, Kobe (JP)

( * ) Notice: Subject to any disclaimer, the term of this patent is extended or adjusted under 35 U.S.C. 154(b) by 416 days.

(21) Appl. No.: 12/079,650

(22) Filed: Mar. 28, 2008

(65) Prior Publication Data

US 2008/0241911 A1    Oct. 2, 2008

(30) Foreign Application Priority Data

Mar. 29, 2007   (JP) .................................. 2007-086957

(51) Int. Cl.
*C12M 1/34* (2006.01)
*G01N 21/00* (2006.01)
*G01N 31/00* (2006.01)
*G01N 33/48* (2006.01)
*G01N 1/00* (2006.01)

(52) U.S. Cl. ... 435/287.1; 422/63; 422/68.1; 422/82.05; 422/82.08; 422/82.09; 356/36; 356/39

(58) Field of Classification Search ...................... 356/36
See application file for complete search history.

(56) References Cited

U.S. PATENT DOCUMENTS

| 5,073,029 | A  | * | 12/1991 | Eberly et al. | ................... | 356/432 |
| 2003/0032193 | A1 | * | 2/2003 | Narisada | ........................... | 436/63 |
| 2005/0002826 | A1 | * | 1/2005 | Oguni et al. | .................... | 422/73 |
| 2006/0029520 | A1 | * | 2/2006 | Tanoshima et al. | ............. | 422/63 |
| 2006/0250604 | A1 | * | 11/2006 | Hamada et al. | ................. | 356/39 |
| 2007/0178009 | A1 | * | 8/2007 | Sakaino et al. | ................. | 422/56 |

FOREIGN PATENT DOCUMENTS

JP   2000-275163   10/2000

* cited by examiner

*Primary Examiner* — Joseph Drodge
*Assistant Examiner* — Jennifer Wecker
(74) *Attorney, Agent, or Firm* — Brinks Hofer Gilson & Lione

(57) ABSTRACT

A sample analyzer for analyzing a biological sample is disclosed that comprising: a measurement specimen preparation section for preparing a measurement specimen by using a reagent and the biological sample; a irradiator for irradiating the measurement specimen with a light; a first light receiving section for receiving a light from the measurement specimen and converting the received light into an electrical signal; a analysis section for analyzing the measurement specimen based on the electrical signal output by the first light receiving section; and a selection section for selecting an intensity of light to be irradiated by the irradiator, wherein the irradiator is configured to irradiate with a light of an intensity corresponding to the light intensity selected by the selection section.

19 Claims, 13 Drawing Sheets

ANALYZER

RELATED APPLICATIONS

This application claims priority under 35 U.S.C. §119 to Japanese Patent Application No. 2007-086957 filed Mar. 29, 2007, the entire contents of which are hereby incorporated by reference.

TECHNICAL FIELD

The present invention relates to analyzers, in particular, to an analyzer for measuring components of a biological sample.

BACKGROUND

An analyzer for measuring components of a biological sample is conventionally known (see e.g., Japanese Laid-Open Patent Publication No. 2000-275163).

Japanese Laid-Open Patent Publication No. 2000-275163 discloses a particle analyzer, including a measurement section for performing measurement through electrical resistance method and a measurement section for performing measurement through flow cytometry method, for measuring platelets in the blood (biological sample).

In the measurement through the flow cytometry method, consideration is made in increasing the irradiating intensity of the irradiator to enhance the measurement accuracy of small particles such as platelet.

However, if the irradiating intensity of the irradiator is increased to enhance the measurement accuracy of small particles such as platelet, it is sometimes difficult to measure other particles (particles larger than platelet) such as white blood cells.

SUMMARY

The scope of the present invention is defined solely by the appended claims, and is not affected to any degree by the statements within this summary.

A first analyzer for analyzing a biological sample embodying features of the present invention includes: a measurement specimen preparation section for preparing a measurement specimen by using a reagent and the biological sample; a irradiator for irradiating the measurement specimen with a light; a first light receiving section for receiving a light from the measurement specimen and converting the received light into an electrical signal; a analysis section for analyzing the measurement specimen based on the electrical signal output by the first light receiving section; and a selection section for selecting an intensity of light to be irradiated by the irradiator, wherein the irradiator is configured to irradiate with a light of an intensity corresponding to the light intensity selected by the selection section.

A second analyzer for analyzing a biological sample embodying features of the present invention includes: a measurement specimen preparation section for preparing a measurement specimen by using a reagent and the biological sample; an irradiator for irradiating the measurement specimen with a light; a light receiving section for receiving a light from the measurement specimen and converting the received light into an electrical signal; an analysis section for analyzing the measurement specimen based on the electrical signal output by the light receiving section; an accepting section for accepting specification of a measurement mode; and a control unit for controlling the irradiator to irradiate the light of the intensity corresponding to the specified measurement mode.

A third analyzer for analyzing a biological sample embodying features of the present invention includes: a measurement specimen preparation section for preparing a measurement specimen by using a reagent and the biological sample; an irradiator for irradiating the measurement specimen with a light; a photoelectric conversion element for photoelectric converting the light from the measurement specimen; an analysis section for analyzing the measurement specimen based on an electrical signal output by the photoelectric conversion element; and an accepting section for accepting specification of a measurement mode to be executed; wherein the measurement specimen preparation section prepares the measurement specimen corresponding to the specified measurement mode; the irradiator irradiates the measurement specimen with the light of intensity corresponding to the specified measurement mode; and the analysis section conducts the analysis corresponding to the specified measurement mode.

DETAILED DESCRIPTION OF THE PREFERRED EMBODIMENTS

The embodiments of the present invention will be described based on the drawings.

Figure 1:
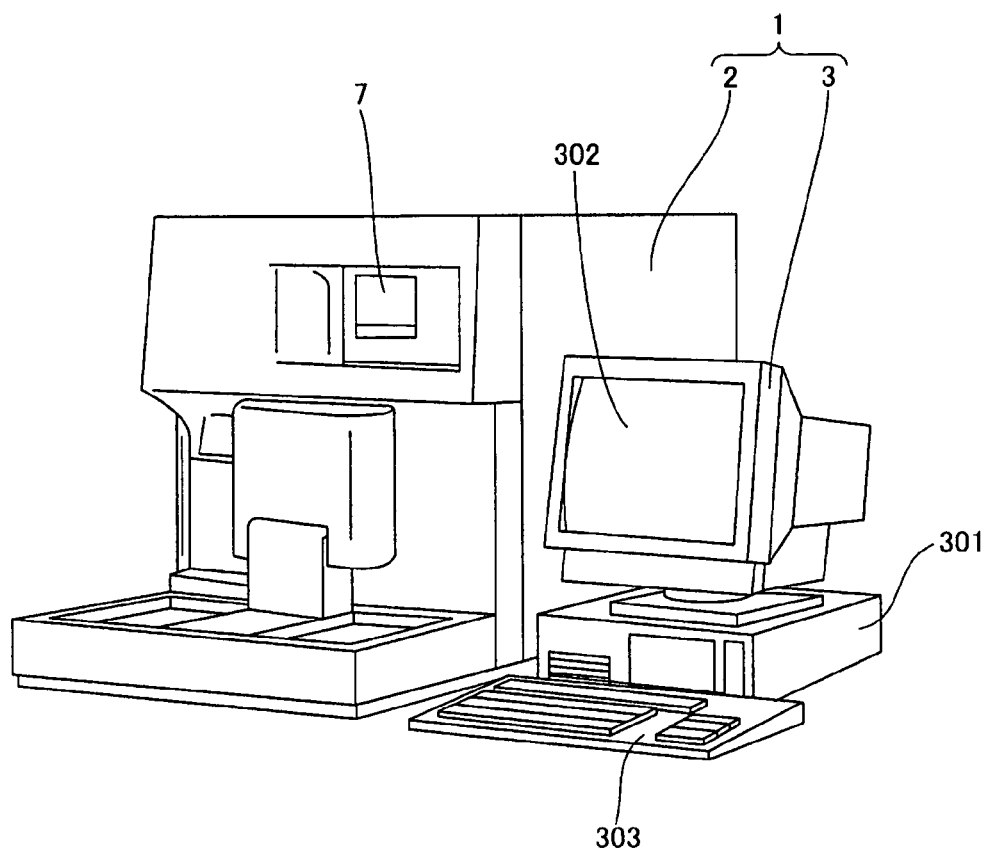
FIG. 1 is a perspective view of a blood analyzer according to one embodiment of the present invention.

FIG. 1 is a perspective view showing a blood analyzer according to one embodiment of the present invention. FIGS.

2 to 6 are views for describing a configuration of the blood analyzer according to one embodiment shown in FIG. 1. The configuration of the blood analyzer 1 according to one embodiment of the present invention will be described with reference to FIGS. 1 to 6. The blood analyzer 1 is configured as a multiple automatic blood cell analyzer for performing blood test, where only the measurement of white blood cells, reticulocytes, and platelets in the blood will be described below.

As shown in FIG. 1, the blood analyzer 1 according to one embodiment of the present invention is configured by a measurement section 2 having a function of measuring the blood or the biological sample, and a data processing section 3 for analyzing the measurement result output from the measurement section 2 and obtaining an analysis result. The measurement section 2 is configured to measure the white blood cells, the reticulocytes, and the platelets in the blood through the flow cytometry method. The flow cytometry method used in this embodiment is a measurement method of forming a sample flow including the measurement specimen and irradiating a laser light onto the sample flow to measure the particles (blood cells) for detecting forward scattered light, lateral scattered light, and lateral fluorescence emitted by the particles (blood cells) in the measurement specimen.

Figure 2:
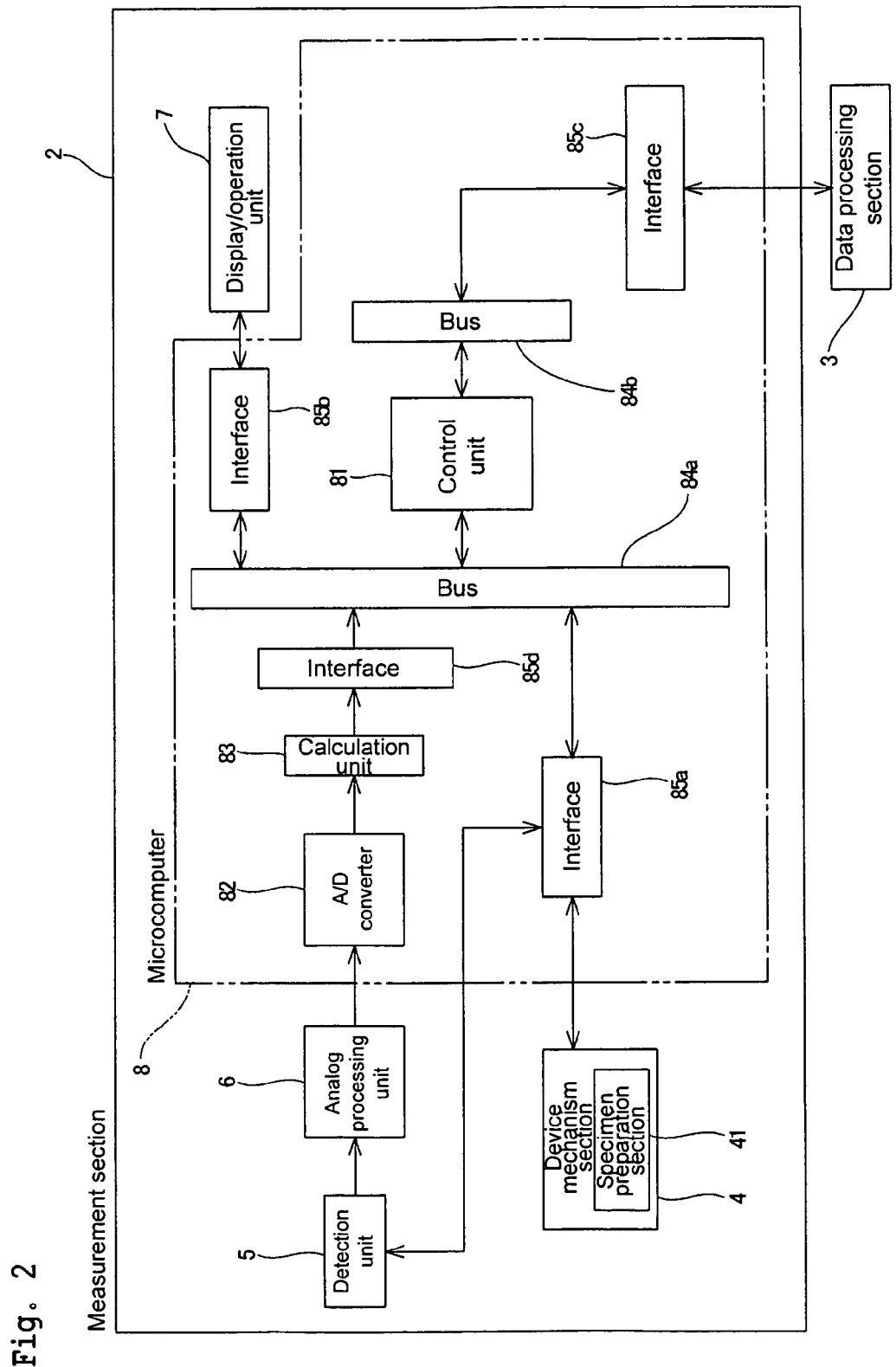
FIG. 2 is a block diagram showing a configuration of the blood analyzer according to the embodiment shown in FIG. 1.

As shown in FIG. 2, the measurement section 2 includes a device mechanism unit 4, a detection unit 5 for measuring the measurement specimen, an analog processing unit 6 on the output of the detection unit 5, a display/operation unit 7, and a microcomputer 8 for controlling the measurement section 2.

Figure 3:
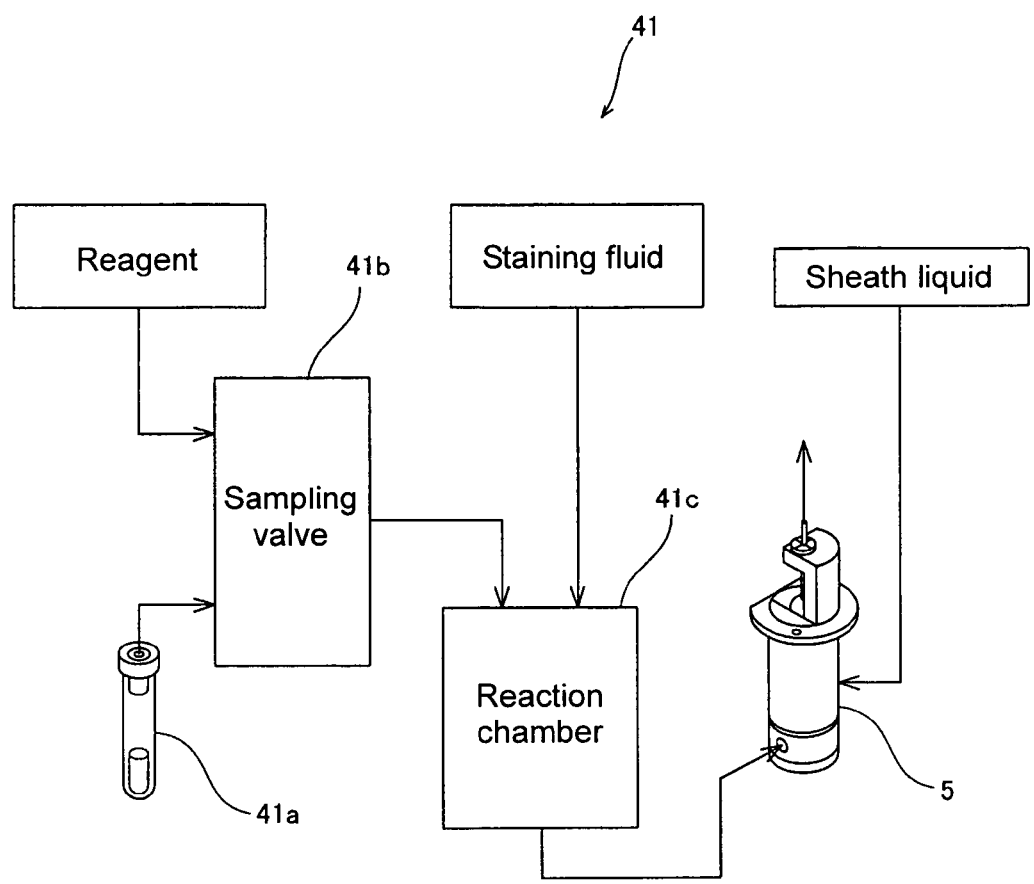
FIG. 3 is a view for describing a specimen preparation section of the blood analyzer according to the embodiment shown in FIG. 1.

The device mechanism unit 4 is arranged with a specimen preparation section 41 for preparing the measurement specimen from a reagent and the blood. The specimen preparation section 41 is arranged to prepare a white blood cell measurement specimen, a reticulocyte measurement specimen, and a platelet measurement specimen. The blood analyzer 1 has a plurality of measurement modes including a white blood cell differentiation measurement mode of preparing and measuring the white blood cell measurement specimen, a reticulocyte measurement mode of preparing and measuring the reticulocyte measurement specimen, and a platelet measurement mode of preparing and measuring the platelet measurement specimen. As shown in FIG. 3, the specimen preparation section 41 includes a blood collection tube 41a filled with a predetermined amount of blood, a sampling valve 41b to which the blood is aspirated, and a reaction chamber 41c. The blood collection tube 41a is replaceable, and is configured to enable replacement of blood. The sampling valve 41b has a function of quantitating the blood of the blood collection tube 41a aspirated by an aspiration pipette (not shown) by a predetermined amount. The sampling valve 41b is configured to mix a predetermined reagent to the aspirated blood. That is, the sampling valve 41b is configured to generate a diluted sample in which a predetermined amount of reagent is mixed to a predetermined amount of blood. The reaction chamber 41c is configured to further mix a predetermined staining fluid to the diluted sample supplied from the sampling valve 41b and react the same for a predetermined time. The specimen preparation section 41 then has a function of preparing a measurement specimen in which the white blood cells are stained and the red blood cells are hemolyzed as a white blood cell measurement specimen. The specimen preparation section 41 also has a function of preparing the measurement specimen in which the reticulocyte is stained as the reticulocyte measurement specimen, and preparing a measurement specimen in which the platelet is stained as the platelet measurement specimen.

The device mechanism unit 4 is configured to supply a white blood cell measurement specimen to a sheath flow cell 503 (see FIG. 4), to be described later, from the specimen preparation section 41 along with sheath liquid in the white blood cell differentiation measurement (hereinafter referred to as "DIFF measurement") mode. The device mechanism unit 4 is configured to supply the reticulocyte measurement specimen to the sheath flow cell 503 from the specimen preparation section 41 along with the sheath liquid in the reticulocyte measurement (hereinafter referred to as "RET measurement") mode. The device mechanism unit 4 is configured to supply the platelet measurement specimen to the sheath flow cell 503 from the specimen preparation section 41 along with the sheath liquid in the platelet measurement (hereinafter referred to as "PLT measurement") mode.

Figure 4:
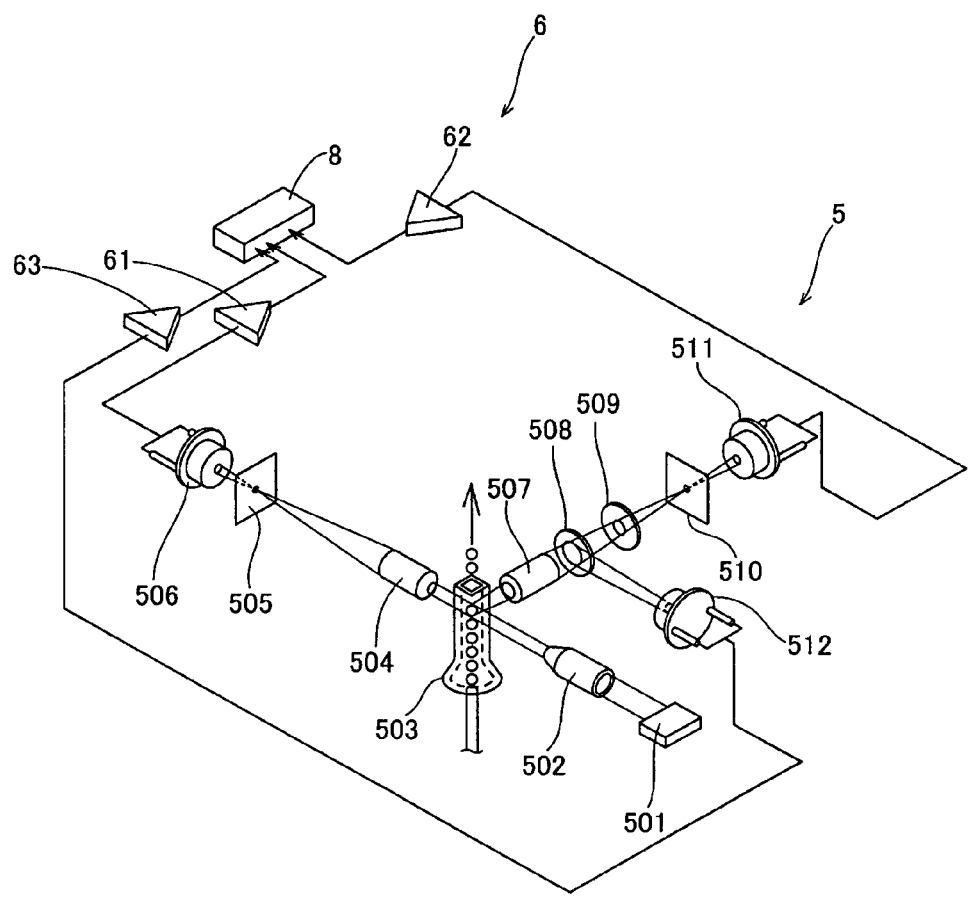
FIG. 4 is a schematic view showing a detection unit of the blood analyzer according to the embodiment shown in FIG. 1.

As shown in FIG. 4, the detection unit 5 includes a light emitting section 501 for irradiating a laser light, an irradiation lens unit 502, a sheath flow cell 503 to be irradiated with the laser light, a light collecting lens 504 arranged on an extending line in a direction the laser light irradiated from the light emitting section 501 advances, a pin hole 505 and a PD (photodiode) 506, a light collecting lens 507 arranged in a direction intersecting the direction the laser light irradiated from the light emitting section 501 advances, a dichroic mirror 508, an optical filter 509, a pin hole 510 and a PD 511, and an APD (avalanche photodiode) 512 arranged on the side of the dichroic mirror 508.

The light emitting section 501 is arranged to irradiate the light on the sample flow including the measurement specimen passing through the inside of the sheath flow cell 503. The irradiation lens unit 502 is arranged to convert the light irradiated from the light emitting section 501 to parallel light. The PD 506 is arranged to receive the forward scattered light irradiated from the sheath flow cell 503. Information on the size of the particle (blood cell) in the measurement specimen can be obtained by the forward scattered light irradiated from the sheath flow cell 503.

The dichroic mirror 508 is arranged to separate the lateral scattered light and the lateral fluorescence irradiated from the sheath flow cell 503. Specifically, the dichroic mirror 508 is arranged to enter the lateral scattered light irradiated from the sheath flow cell 503 to the PD 511 and to enter the lateral fluorescence irradiated from the sheath flow cell 503 to the APD 512. The PD 511 is arranged to receive the lateral scattered light. Internal information such as the size of the core of the particle (blood cell) in the measurement specimen can be obtained by the lateral scattered light irradiated from the sheath flow cell 503. The APD 512 is arranged to receive the lateral fluorescence. Information on the degree of stain of the particle (blood cell) in the measurement specimen can be obtained by the lateral fluorescence irradiated from the sheath flow cell 503. The PDs 506, 511 and the APD 512 respectively have functions of converting the received light signal to an electrical signal.

Figure 5:
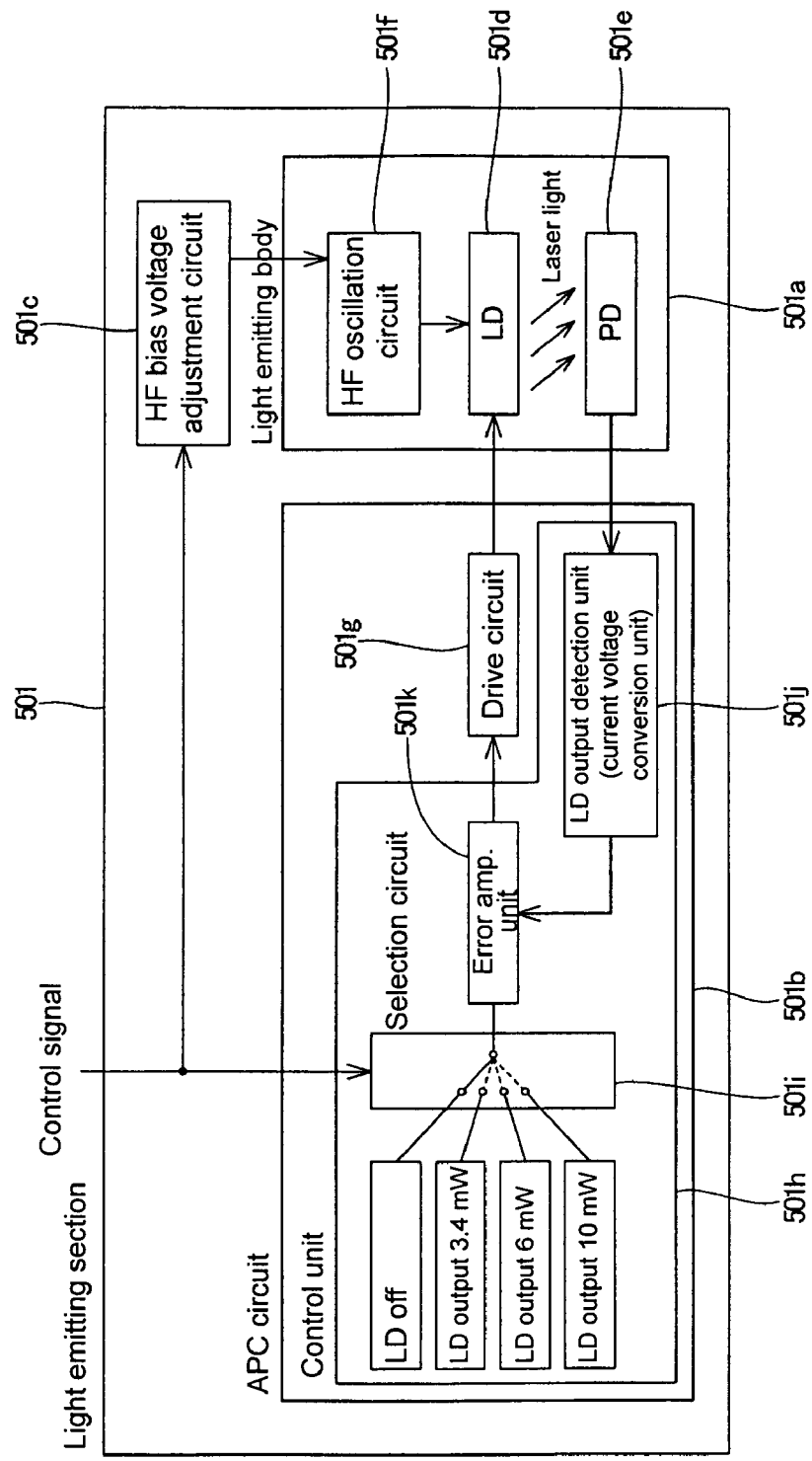
FIG. 5 is a block diagram showing a configuration of a light emitting section of the blood analyzer according to the embodiment shown in FIG. 1.

In the present embodiment, the light emitting section 501 is configured to irradiate light at an output of 3.4 mW in the DIFF measurement mode. The light emitting section 501 is configured to irradiate light at an output of 6 mW in the RET measurement mode. The light emitting section 501 is configured to irradiate light at an output of 10 mW in the PLT measurement mode. As shown in FIG. 5, the light emitting section 501 includes a light emitting body 501a, an APC (Automatic Power Control) circuit 501b for controlling the irradiating intensity irradiated from the light emitting body 501a, and a high frequency bias voltage adjustment circuit 501c.

In the present embodiment, the light emitting body 501a includes an LD (laser diode) 501d for irradiating light to the sample flow of the sheath flow cell 503, a PD 501e for receiving the light irradiated from the LD 501d, and a high frequency oscillation circuit 501f. The PD 501e has a function of converting the received light signal to an electrical signal. The high frequency oscillation circuit 501f is arranged to generate a signal superimposed on a drive current supplied to the LD 501d. That is, the high frequency oscillation circuit 501f is arranged to have the light irradiated from the LD 501d in multimode in which a great number of oscillation wavelengths are present.

In the present embodiment, the APC circuit 501b includes a drive circuit 501g for supplying the drive current to the LD 501d, and a control unit 501h for controlling the drive current supplied from the drive circuit 501g to the LD 501d. The control unit 501h includes a selection circuit 501i, an LD output detection unit 501j or a current-voltage conversion unit, and an error amplification unit 501k. A control signal from the microcomputer 8 (see FIG. 2) is provided to the selection circuit 501i. The selection circuit 501i is arranged to select the irradiating intensity irradiated from the LD 501d according to the control signal. Specifically, the selection circuit 501i is configured to set the output of the LD 501d to 3.4 mW in the DIFF measurement mode. The selection circuit 501i is configured to set the output of the LD 501d to 6 mW in the RET measurement mode. The selection circuit 501i is configured to set the output of the LD 501d to 10 mW in the PLT measurement mode. The selection circuit 501i is configured to set the LD 501d in the OFF state other than in the measurement modes.

In the present embodiment, the LD output detection unit 501j is arranged to detect the irradiating intensity irradiated from the LD 501d based on the electrical signal output from the PD 501e. The error amplification unit 501k is arranged to compare the irradiating intensity irradiated from the LD 501d detected by the LD output detection unit 501j and the irradiating intensity selected by the selection circuit 501i, and control the drive circuit 501g so that the irradiating intensity irradiated from the LD 501d approaches the irradiating intensity selected by the selection circuit 501i.

In the present embodiment, the control signal from the microcomputer 8 (see FIG. 2) is provided to the high frequency bias voltage adjustment circuit 501c. The high frequency bias voltage adjustment circuit 501c is arranged to adjust the bias voltage to be supplied to the high frequency oscillation circuit 501f according to the control signal. Specifically, the high frequency bias voltage adjustment circuit 501c is configured so that the bias voltage becomes larger as the output of the LD 501d becomes larger.

As shown in FIG. 4, the analog processing unit 6 includes amplifiers 61, 62, and 63. The amplifiers 61, 62, and 63 are respectively arranged to perform amplification and waveform processing on the electrical signal output from the PDs 506, 511 and the APD 512.

As shown in FIG. 2, the microcomputer 8 includes a control unit 81 with a control processor and a memory for operating the control processor, an A/D converter 82 for converting the signal output from the analog processing unit 6 to a digital signal, and a calculation unit 83 for performing a predetermined process on the digital signal output from the A/D converter 82. The control unit 81 has a function of controlling the device mechanism unit 4 and the detection unit 5 by way of a bus 84a and an interface 85a. The control unit 81 is connected to the display/operation unit 7 by way of the bus 84a and the interface 85b, and is connected to the data processing section 3 by way of a bus 84b and an interface 85c.

The calculation unit 83 has a function of outputting the calculation result to the control unit 81 via the interface 85d and the bus 84a. The control unit 81 also has a function of transmitting the calculation result (measurement data) to the data processing section 3.

Figure 6:
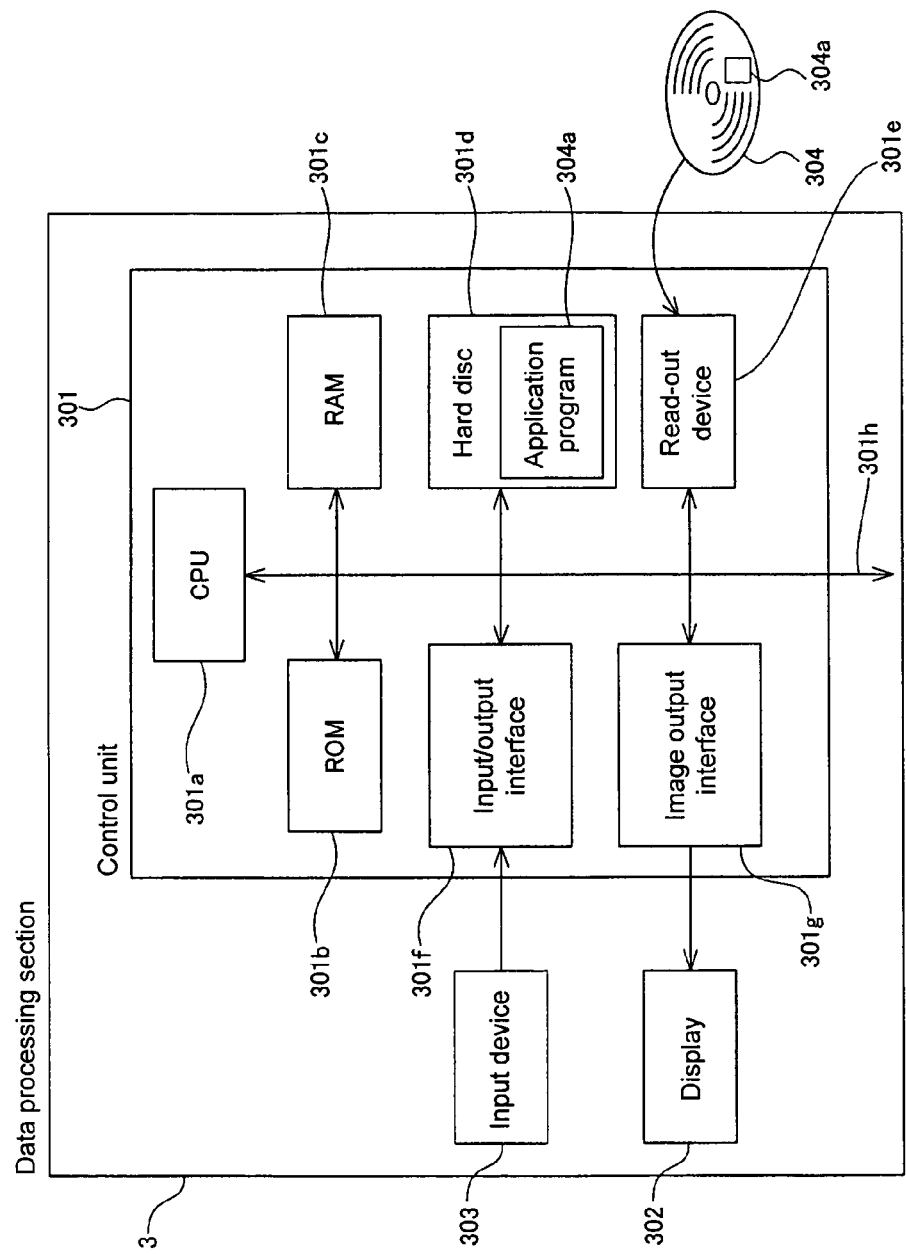
FIG. 6 is a block diagram showing a configuration of a data processing section of the blood analyzer according to the embodiment shown in FIG. 1.

As shown in FIG. 1, the data processing section 3 is configured by a personal computer (PC), and has a function of analyzing the measurement data of the measurement section 2 and displaying the analysis result. The data processing section 3 includes a control unit 301, a display 302, and an input device 303. The control unit 301 has a function of transmitting a measurement start signal including measurement mode information and a shutdown signal to the measurement section 2. As shown in FIG. 6, the control unit 301 is configured by a CPU 301a, a ROM 301b, a RAM 301c, a hard disc 301d, a read-out device 301e, an input/output interface 301f, and an image output interface 301g. The CPU 301a, the ROM 301b, the RAM 301c, the hard disc 301d, the read-out device 301e, the input/output interface 301f, and the image output interface 301g are connected by a bus 301h.

The CPU 301a is arranged to execute the computer program stored in the ROM 301b and the computer program loaded in the RAM 301c. ROM 301b is configured by mask ROM, PROM, EPROM, EEPROM, and the like, and is recorded with the computer program to be executed by the CPU 301a, data used for the same, and the like.

The RAM 301c is configured by SRAM, DRAM, or the like. The RAM 301c is used to read out the computer program recorded on the ROM 301b and the hard disc 301d. When executing such computer program, the RAM 301c is used as a work region of the CPU 301a.

The hard disc 301d is installed with various computer programs for the CPU 301a to execute such as operating system and application program, and data used in execution of the computer programs. The application program 304a to be described later is also installed in the hard disc 301d.

The read-out device 301e is configured by flexible disc drive, CD-ROM drive, DVD-ROM, or the like, and reads computer program or data recorded on a portable recording medium 304. The application program 304a for the computer to realize a predetermined function is stored in the portable recording medium 304, and the computer serving as the data processing section 3 reads out the application program 304a from the portable recording medium 304 and installs the application program 304a in the hard disc 301d.

The application program 304a is not only provided by the portable recording medium 304, but also provided through the electric telecommunication line from the external equipment communicably connected to the data processing section 3 by the electric telecommunication line (wired or wireless). For instance, the application program 304a may be stored in the hard disc of the server computer on the Internet, and the data processing section 3 may download the application program 304a by accessing the server computer, and install the application program 304a in the hard disc 301d.

The operating system that provides graphical user interface environment such as Windows (Registered trademark) manufactured and sold by US Microsoft Co., Ltd. is installed in the hard disc 301d. In the following description, the application program 304a according to the present embodiment operates on the operating system.

The input/output interface 301f is configured by serial interface such as USB, IEEE1394, RS-232C; parallel interface such as SCSI, IDE, IEEE1284; analog interface including D/A converter, A/D converter and the like. The input device 303 including keyboard and mouse is connected to the input/output interface 301f, so that the user can use the input device 303 to input data to the data processing section 3. The input device 303 is used to input specification of the measurement mode. Specifically, the user uses the input device 303 to specify whether or not to perform each of the DIFF measurement, the RET measurement, and the PLT measurement on a predetermined blood, and the control unit 301 accepts the result of specification.

The image output interface 301g is connected to the display 302 configured by LCD, CRT, or the like, and outputs an image signal corresponding to the image data provided from the CPU 301a to the display 302. The display 302 displays the image (screen) according to the input image signal.

Figure 7:
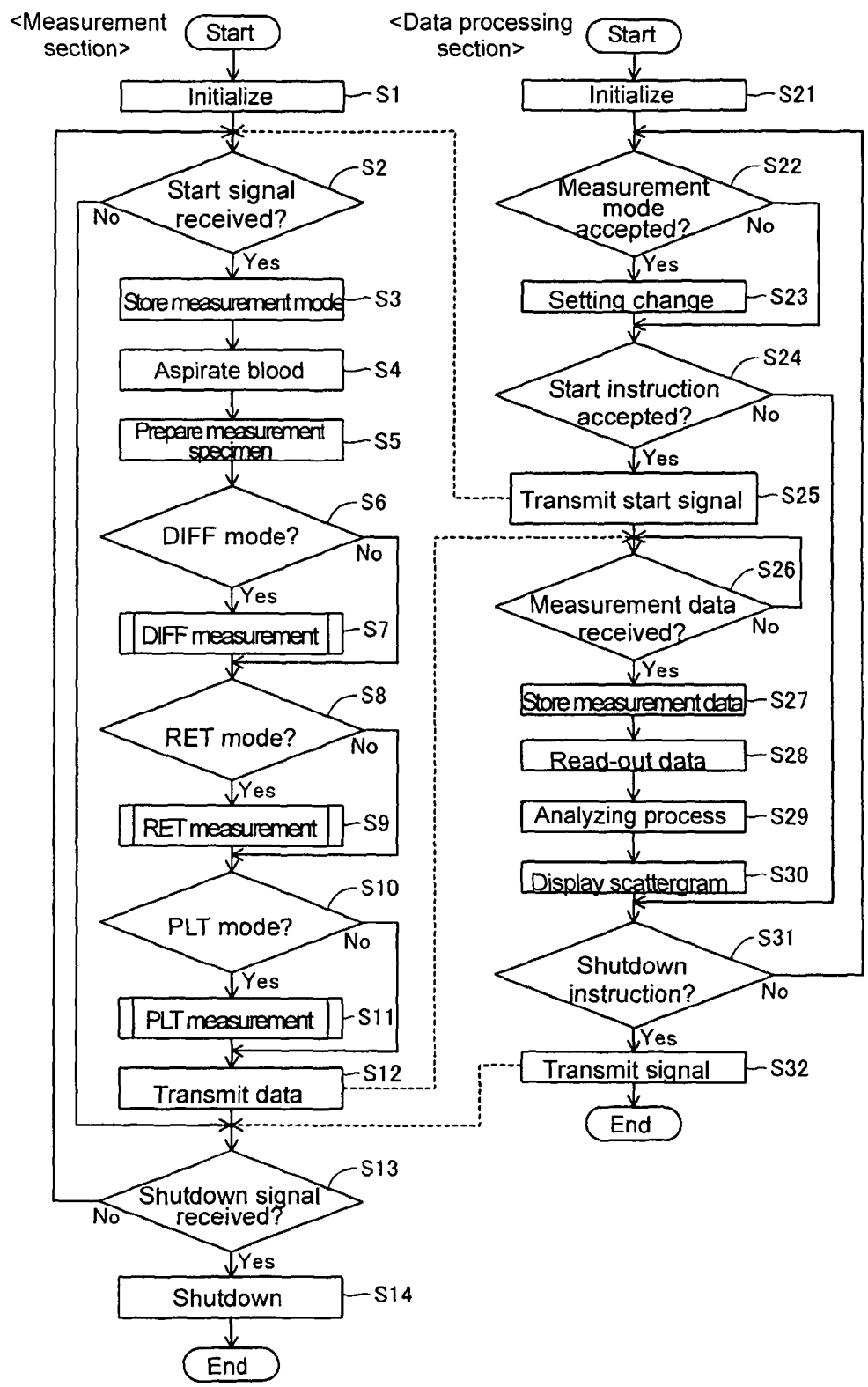
FIG. 7 is a flowchart describing the blood analyzing operation of the blood analyzer according to the embodiment of the present invention.

FIG. 7 is a flowchart describing the blood analyzing operation of the blood analyzer according to one embodiment of the present invention. The blood analyzing operation of the blood analyzer 1 according to one embodiment of the present invention will be described with reference to FIGS. 1 to 3, 6, and 7.

First, in the measurement section 2, when the main switch (not shown) of the measurement section 2 (see FIG. 1) is turned ON in step S1 of FIG. 7, the control unit 81 (see FIG. 2) is initialized and the operation check of each unit of the measurement section 2 is performed. The process thereafter proceeds to step S2.

In the data processing section 3, in step S21 of FIG. 7, the control unit 301 (see FIG. 6) is initialized (initialization of program). The menu screen (not shown) is displayed on the display 302 (see FIG. 1) by the control unit 301. The menu screen is a screen for the user to select whether or not to set each of the DIFF measurement mode, the RET measurement mode, and the PLT measurement mode. Options corresponding to each of the DIFF measurement mode, the RET measurement mode, and the PLT measurement mode are displayed on the menu screen. The user selects arbitrary one or a plurality of options from the above options using the input device 303. The measurement mode to be executed on the blood sample to be analyzed is specified. The menu screen is a screen for accepting measurement start instruction and shutdown instruction from the user.

In step S22, determination is made on whether or not the input (specification) of the measurement mode is accepted by the control unit 301. If determined that the input of the measurement mode is accepted by the control unit 301, setting change of the measurement mode is performed by the control unit 301 in step S23. Specifically, the measurement mode accepted by the input device 303 (see FIG. 1) is set. If determined that the input of the measurement mode is accepted by the control unit 301, the process proceeds to step S24.

In step S24, determination is made on whether or not the measurement start instruction is accepted by the control unit 301. If determined that the measurement start instruction is accepted by the control unit 301, the process proceeds to step S25. If determined that the measurement start instruction is not accepted by the control unit 301, the process proceeds to step S31. In step S25, the measurement start signal including the measurement mode information is transmitted to the measurement section 2 by the control unit 301. The process thereafter proceeds to step S26.

In the measurement section 2, determination is made on whether or not the measurement start signal from the data processing section 3 is received by the control unit 81 in step S2. If determined that the measurement start signal is received by the control unit 81, the process proceeds to step 3. If determined that the measurement start signal is not received by the control unit 81, the process proceeds to step S13.

In step S3, the measurement mode in the measurement start information is stored by the control unit 81. Specifically, whether or not the DIFF measurement mode, the RET measurement mode, and the PLT measurement mode is set is stored. In step S4, the blood for the set measurement mode is aspirated. Specifically, the blood in the blood collection tube 11 (see FIG. 3) is aspirated to the sampling valve 12 (see FIG. 3) by the aspiration pipette. Subsequently, in step S5, the measurement specimen for the set measurement mode is prepared. Specifically, a predetermined reagent is supplied to the sampling valve 12, whereby a predetermined amount of blood and a predetermined amount of reagent are mixed to produce diluted sample. The diluted sample is then supplied to the reaction chamber 13 (see FIG. 3), and a predetermined amount of staining fluid is supplied to the reaction chamber 13. The diluted sample and the staining fluid are then mixed and reacted for a predetermined time. The measurement specimen corresponding to each measurement mode is thereby prepared from one blood sample contained in the blood collecting tube 11. For instance, when all the measurement modes of the DIFF measurement, the RET measurement, and the PLT measurement are set for the analysis on the blood sample contained in the blood collecting tube 11, the blood necessary for preparing the measurement specimen of each measurement mode is divided from the blood contained in the blood collecting tube 11, and the divided blood is mixed with the predetermined reagent and the staining fluid to prepare the measurement specimen for each measurement mode measurement.

In step S6, determination is made on whether or not the DIFF measurement mode is set by the control unit 81. If determined that the DIFF measurement mode is set by the control unit 81, the DIFF measurement is performed in step S7. The operation of the DIFF measurement will be described later in detail. If determined that the DIFF measurement mode is not set by the control unit 81, the process proceeds to step S8.

In step S8, determination is made on whether or not the RET measurement mode is set by the control unit 81. If determined that the RET measurement mode is set by the control unit 81, the RET measurement is performed in step S9. The operation of the RET measurement will be described later in detail. If determined that the RET measurement mode is not set by the control unit 81, the process proceeds to step S10.

In step S10, determination is made on whether or not the PLT measurement mode is set by the control unit 81. If determined that the PLT measurement mode is set by the control unit 81, the PLT measurement is performed in step S11. The operation of the PLT measurement will be described later in detail. If determined that the PLT measurement mode is not set by the control unit 81, the process proceeds to step S12.

In step S12, the measurement result (measurement data) of the set measurement mode is transmitted to the data processing section 3 via the bus 84b (see FIG. 3) and the interface 85c (see FIG. 3) by the control unit 81. The process thereafter proceeds to step S13.

In the data processing section 3, determination is made on whether or not the measurement result (measurement data) is received from the measurement section 2 by the control unit 301 in step S26. If determined that the measurement data is received by the control unit 301, the process proceeds to step S27. If determined that the measurement data is not received by the control unit 301, step S26 is repeated until determined that the measurement data is received.

Figure 8:
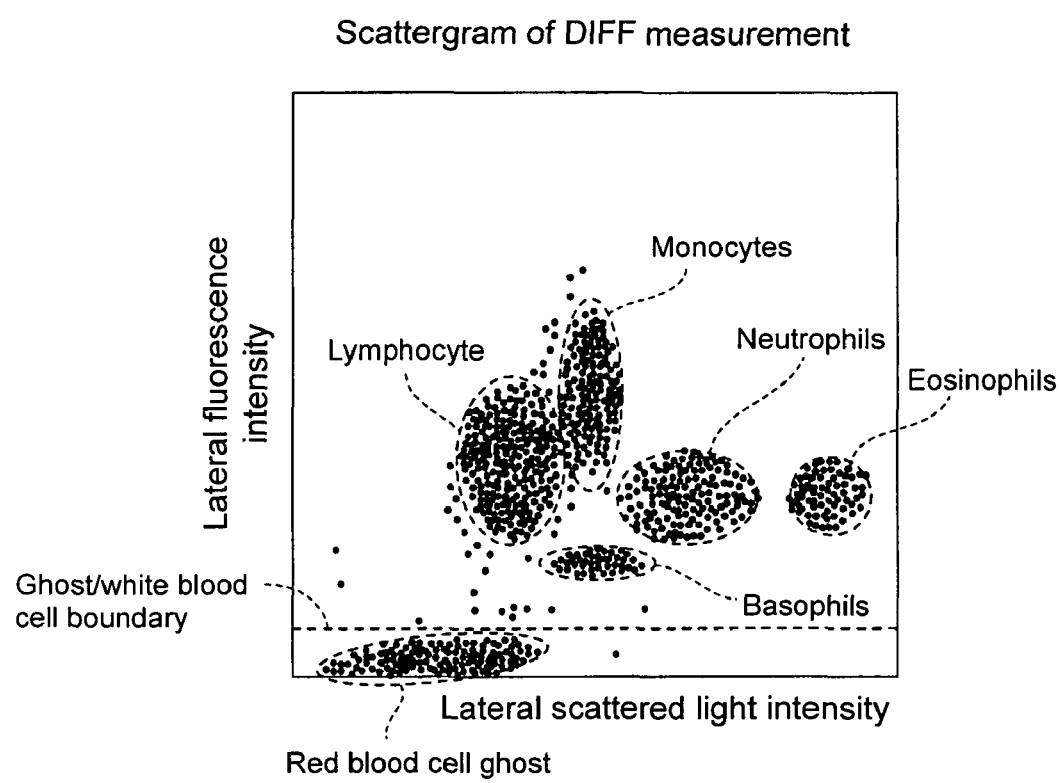
FIG. 8 is a scattergram showing the result of DIFF measurement of the blood analyzer according to the embodiment of the present invention.
Figure 9:
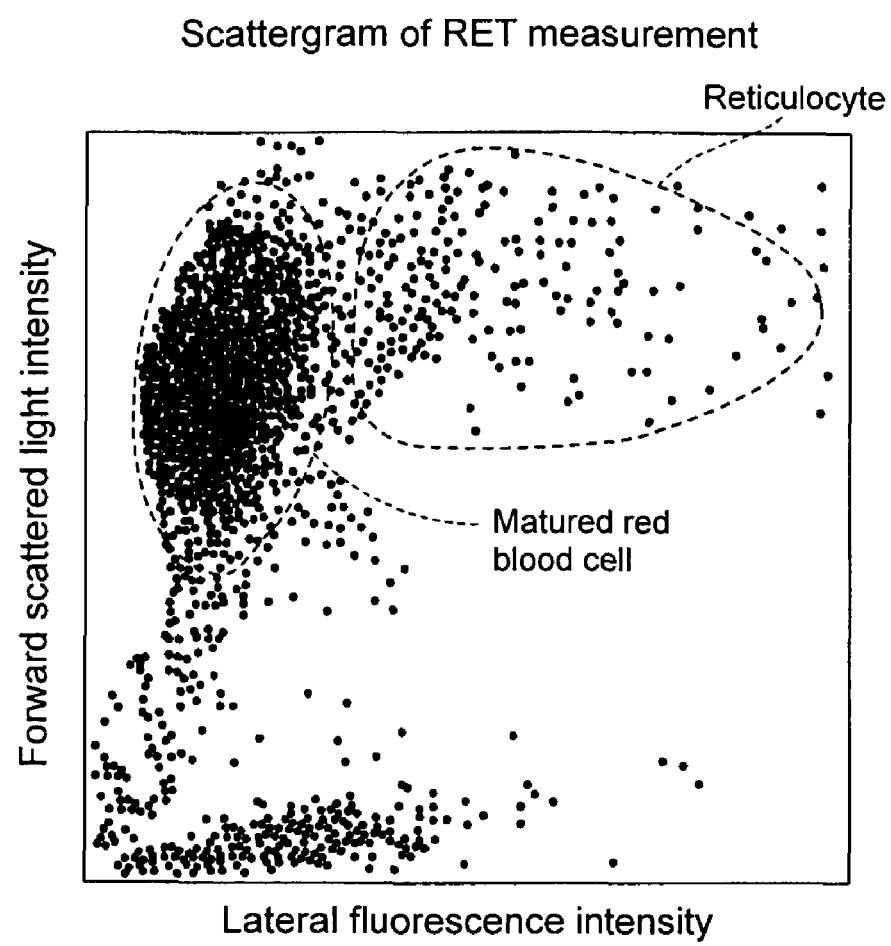
FIG. 9 is a scattergram showing the result of RET measurement of the blood analyzer according to the embodiment of the present invention.
Figure 10:
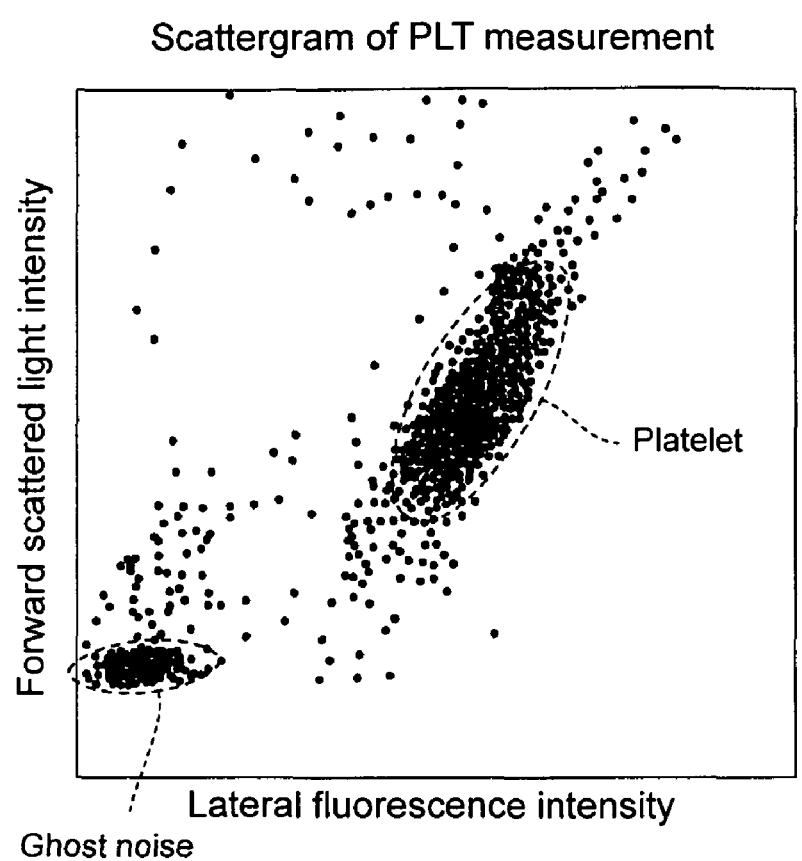
FIG. 10 is a scattergram showing the result of PLT measurement of the blood analyzer according to the embodiment of the present invention.

In step S27, the received measurement data is stored in the hard disc 301d (see FIG. 6) by the CPU 301a (see FIG. 6). Thereafter, in step S28, the measurement data is read out to the RAM 301c (see FIG. 6) by the CPU 301a. In step S29, the measurement data read out to the RAM 301c is performed with analyzing process by the CPU 301a. In step S30, the analyzing processed data is output to the display 302 via the image output interface 301g by the CPU 301a. Specifically, when the DIFF measurement is performed in step S7, the analyzing process of classifying and counting the lymphocytes, the monocytes, the neutrophils, the basophils, and the eosinophils in the blood is performed, and thereafter a scattergram as shown in FIG. 8 is displayed. When the RET measurement is performed in step S9, the analyzing process of classifying and counting the reticulocyte in the blood is performed, and thereafter a scattergram as shown in FIG. 9 is displayed. When the PLT measurement is performed in step S11, the analyzing process of classifying and counting the platelet in the blood is performed, and thereafter, a scattergram as shown in FIG. 10 is displayed. With the display of scattergrams as shown in FIGS. 8 to 10, the measurement result measured with the irradiating intensity suited to each measuring target can be visibly recognized by the user in each measurement mode.

In step S31, determination is made on whether or not the shutdown instruction is accepted by the control unit 301. If determined that the shutdown instruction is accepted by the control unit 301, the shutdown signal is transmitted to the measurement section 2 in step S32, and the process is terminated. If determined that the shutdown instruction is not accepted by the control unit 301, the process returns to step S22.

In the measurement section 2, in step S13, determination is made on whether or not the shutdown signal is received from the data processing section 3 by the control unit 81. If determined that the shutdown signal is received by the control unit 81, the measurement section 2 is shutdown in step S14, and the process is terminated. If determined that the shutdown signal is not received by the control unit 81 in step S13, the process returns to step S2.

Figure 11:
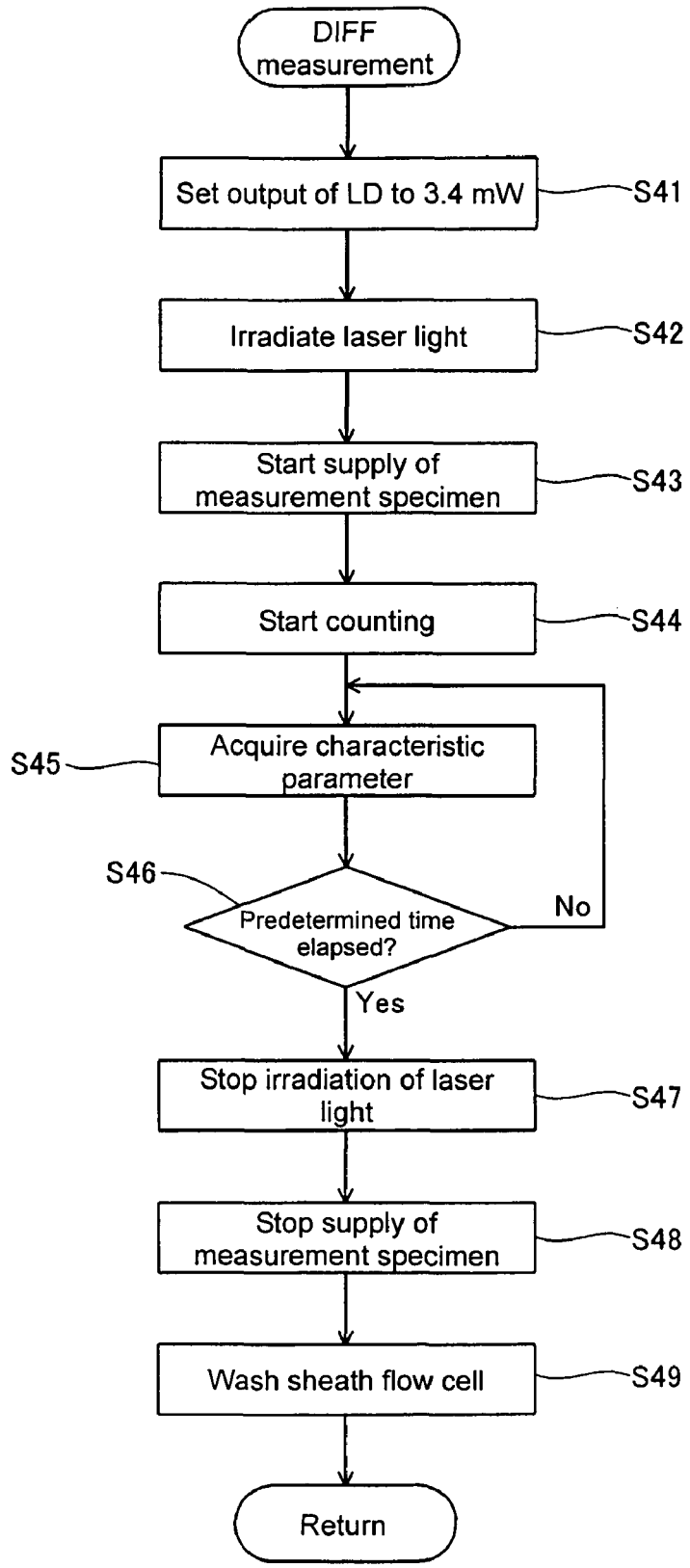
FIG. 11 is a flowchart for describing the operation of the DIFF measurement of the blood analyzer according to one embodiment of the present invention.

FIG. 11 is a flowchart for describing the operation in the DIFF measurement of the blood analyzer according to one embodiment of the present invention. The details of the DIFF measurement of step S7 shown in FIG. 7 will be described with reference to FIGS. 2, 4, 5, and 11.

First, in step S41 of FIG. 11, the output of the LD 501d (see FIG. 5) is set to 3.4 mW by the control unit 81 (see FIG. 2). In step S42, the laser light is irradiated on the sheath flow cell 503 (see FIG. 4). Specifically, the control signal is provided from the control unit 81 to the selection circuit 501i (see FIG. 5). The control unit 501h (see FIG. 5) controls the drive circuit 501g (see FIG. 5) to output the drive current of having the output of the LD 501d to 3.4 mW. In this case, a predetermined bias voltage is supplied to the high frequency oscillation circuit 501f by providing the control signal from the control unit 81 to the high frequency bias voltage adjustment circuit 501c. The signal corresponding to the drive current is superimposed from the high frequency oscillation circuit 501f on the drive current output from the drive circuit 501g.

In step S43, the white blood cell measurement specimen is supplied with the sheath liquid to the sheath flow cell 503 by the control unit 81. In step S44, the counting is started by the control unit 81. When laser light is irradiated on the white blood cells passing through the sheath flow cell 503, the forward scattered light, the lateral scattered light, and the lateral fluorescence are emitted from the white blood cells. The lateral scattered light and the lateral fluorescence emitted from the white blood cells are respectively received by the PD 511 and the APD 512 (see FIG. 4), and converted to an analog electrical signal. The electrical signal of the lateral scattered light and the electrical signal of the lateral fluorescence are respectively transmitted to the A/D converter 82 (see FIG. 2) through the amplifiers 62 and 63 (see FIG. 4).

In step S45, the characteristic parameter of the lateral scattered light and the lateral fluorescence is acquired by the calculation unit 83 (see FIG. 2). In step S46, determination is made on whether or not a predetermined time has elapsed from the start of counting by the control unit 81. If determined that the predetermined time has not elapsed from the start of counting by the control unit 81, the process returns to step S45. That is, the operation of step S45 is repeatedly performed until the predetermined time has elapsed from the start of counting. If determined that the predetermined time has elapsed from the start of counting in step S46, irradiation of the laser light is stopped in step S47. Specifically, the control signal is provided from the control unit 81 to the selection circuit 501i, whereby the control unit 501h controls the drive circuit 501g to turn OFF the LD 501d. That is, the drive current supplied from the drive circuit 501g to the LD 501d is stopped by the control unit 501h. In step S48, supply of white blood cell measurement specimen is stopped. Thereafter, in step S49, the sheath flow cell 503 is washed.

Figure 12:
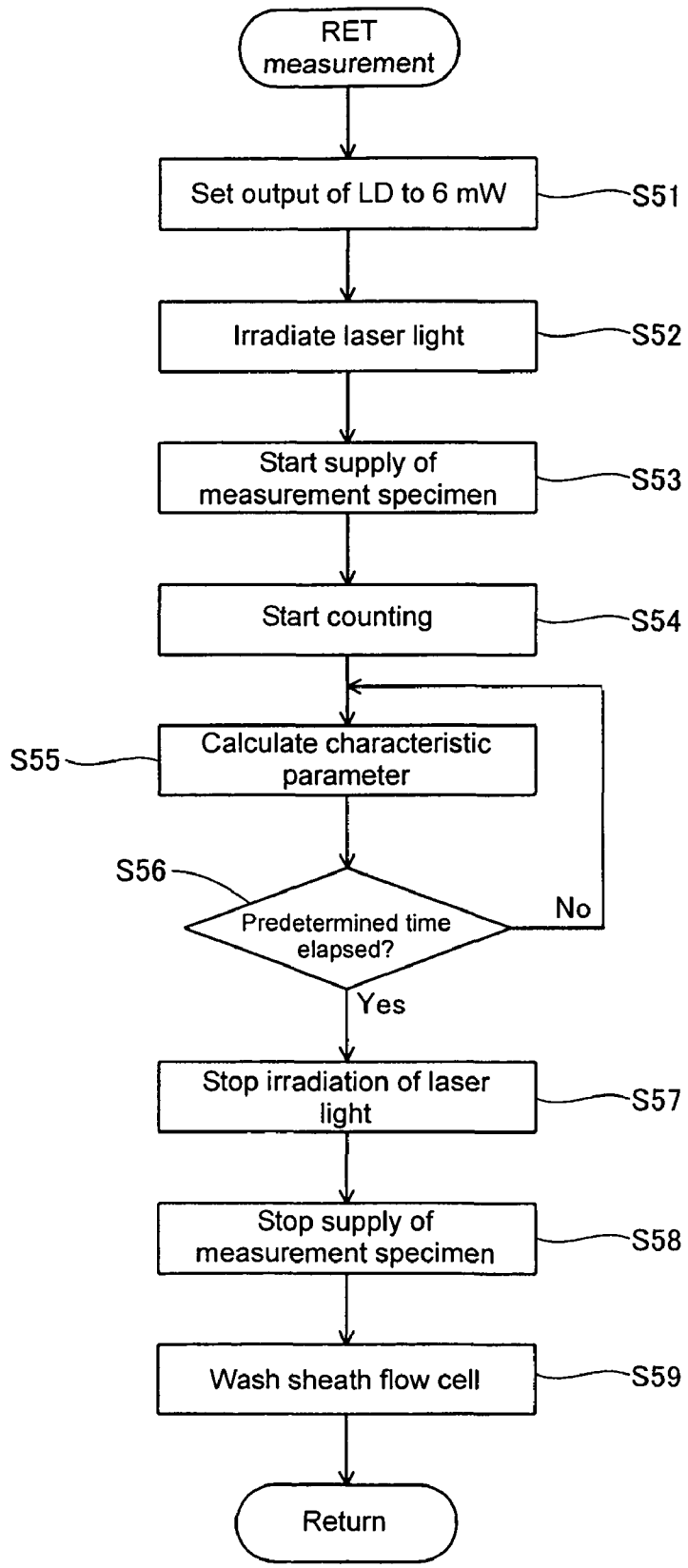
FIG. 12 is a flowchart for describing the operation of the RET measurement of the blood analyzer according to one embodiment of the present invention.

FIG. 12 is a flowchart for describing the operation in the RET measurement of the blood analyzer according to one embodiment of the present invention. The details of the RET measurement of step S9 shown in FIG. 7 will be described with reference to FIGS. 2, 4, 5, and 12.

In step S51 of FIG. 12, the output of the LD 501d (see FIG. 5) is set to 6 mW by the control unit 81 (see FIG. 2). In step S52, the laser light is irradiated on the sheath flow cell 503 (see FIG. 4). Specifically, the control signal is provided from the control unit 81 to the selection circuit 501i (see FIG. 5). The control unit 501h (see FIG. 5) controls the drive circuit 501g (see FIG. 5) to output the drive current of having the output of the LD 501d to 6 mW. In this case, a predetermined bias voltage is supplied to the high frequency oscillation circuit 501f by providing the control signal from the control unit 81 to the high frequency bias voltage adjustment circuit 501c. The signal corresponding to the drive current is superimposed from the high frequency oscillation circuit 501f on the drive current output from the drive circuit 501g.

In step S53, the reticulocyte measurement specimen is supplied with the sheath liquid to the sheath flow cell 503 by the control unit 81. In step S54, the counting is started by the control unit 81. When laser light is irradiated on the reticulocyte passing through the sheath flow cell 503, the forward scattered light, the lateral scattered light, and the lateral fluorescence are emitted from the reticulocyte. The forward scattered light and the lateral fluorescence emitted from the reticulocyte are respectively received by the PD 506 and the APD 512 (see FIG. 4), and converted to an analog electrical signal. The electrical signal of the forward scattered light and the electrical signal of the lateral fluorescence are respectively transmitted to the A/D converter 82 (see FIG. 2) through the amplifiers 61 and 63 (see FIG. 4).

In step S55, the characteristic parameter of the forward scattered light and the lateral fluorescence is acquired by the calculation unit 83 (see FIG. 2). In step S56, determination is made on whether or not a predetermined time has elapsed from the start of counting by the control unit 81. If determined that the predetermined time has not elapsed from the start of counting by the control unit 81, the process returns to step S55. That is, the operation of step S55 is repeatedly performed until the predetermined time has elapsed from the start of counting. If determined that the predetermined time has elapsed from the start of counting in step S56, irradiation of the laser light is stopped in step S57. Specifically, the control signal is provided from the control unit 81 to the selection circuit 501*i*, whereby the control unit 501*h* controls the drive circuit 501*g* to turn OFF the LD 501*d*. That is, the drive current supplied from the drive circuit 501*g* to the LD 501*d* is stopped by the control unit 501*h*. In step S58, supply of reticulocyte measurement specimen is stopped. Thereafter, in step S59, the sheath flow cell 503 is washed.

Figure 13:
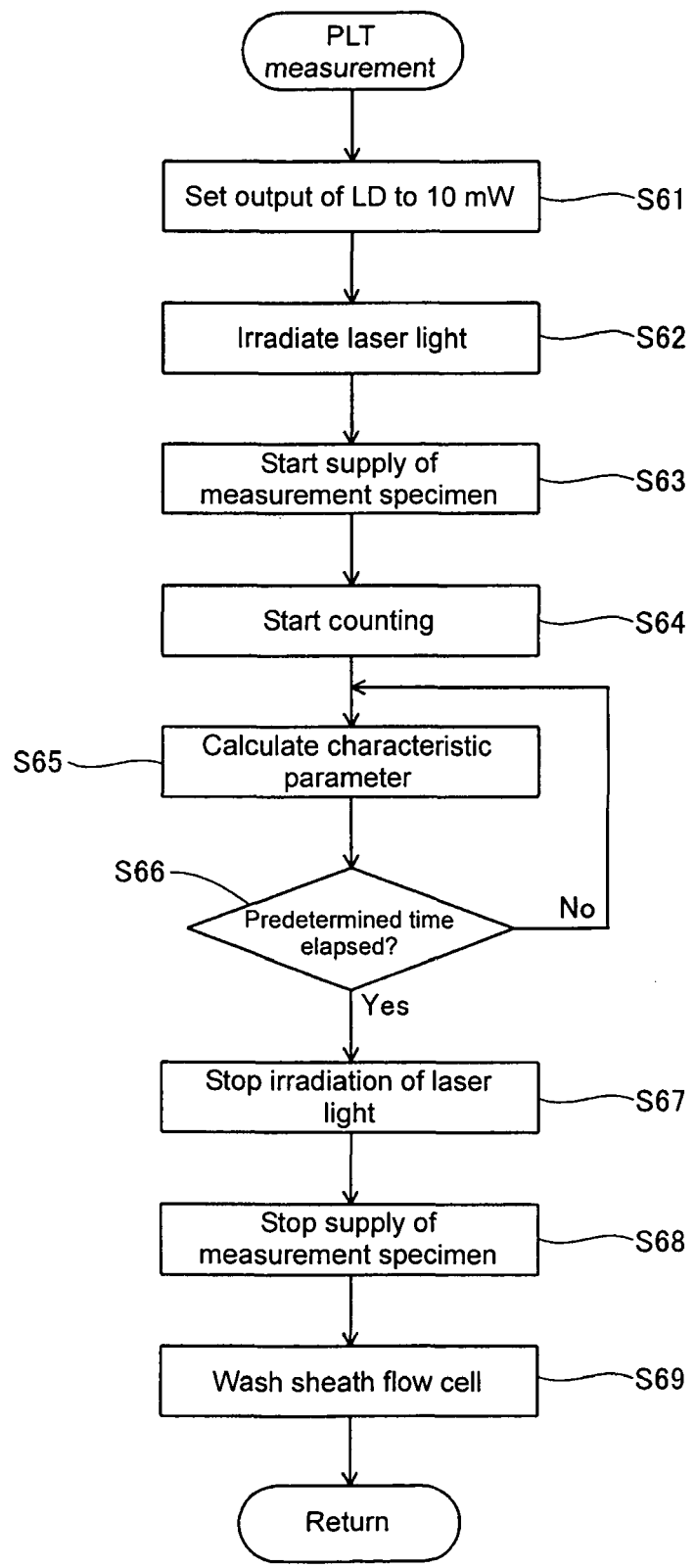
FIG. 13 is a flowchart for describing the operation of the PLT measurement of the blood analyzer according to one embodiment of the present invention.

FIG. 13 is a flowchart for describing the operation in the PLT measurement of the blood analyzer according to one embodiment of the present invention. The details of the PLT measurement of step S11 shown in FIG. 7 will be described with reference to FIGS. 2, 4, 5, and 13.

In step S61 of FIG. 13, the output of the LD501*d* (see FIG. 5) is set to 10 mW by the control unit 81 (see FIG. 2). In step S62, the laser light is irradiated on the sheath flow cell 503 (see FIG. 4). Specifically, the control signal is provided from the control unit 81 to the selection circuit 501*i* (see FIG. 5). The control unit 501*h* (see FIG. 5) controls the drive circuit 501*g* (see FIG. 5) to output the drive current of having the output of the LD 501*d* to 10 mW. In this case, a predetermined bias voltage is supplied to the high frequency oscillation circuit 501*f* by providing the control signal from the control unit 81 to the high frequency bias voltage adjustment circuit 501*c*. The signal corresponding to the drive current is superimposed from the high frequency oscillation circuit 501*f* on the drive current output from the drive circuit 501*g*.

In step S63, the platelet measurement specimen is supplied with the sheath liquid to the sheath flow cell 503 by the control unit 81. In step S64, the counting is started by the control unit 81. When laser light is irradiated on the platelet passing through the sheath flow cell 503, the forward scattered light, the lateral scattered light, and the lateral fluorescence are emitted from the platelet. The forward scattered light and the lateral fluorescence emitted from the platelet are respectively received by the PD 506 and the APD 512 (see FIG. 4), and converted to an analog electrical signal. The electrical signal of the forward scattered light and the electrical signal of the lateral fluorescence are respectively transmitted to the A/D converter 82 (see FIG. 2) through the amplifiers 61 and 63 (see FIG. 4).

In step S65, the characteristic parameter of the forward scattered light and the lateral fluorescence is acquired by the calculation unit 83 (see FIG. 2). In step S66, determination is made on whether or not a predetermined time has elapsed from the start of counting by the control unit 81. If determined that the predetermined time has not elapsed from the start of counting by the control unit 81, the process returns to step S65. That is, the operation of step S65 is repeatedly performed until the predetermined time has elapsed from the start of counting. If determined that the predetermined time has elapsed from the start of counting in step S66, irradiation of the laser light is stopped in step S67. Specifically, the control signal is provided from the control unit 81 to the selection circuit 501*i*, whereby the control unit 501*h* controls the drive circuit 501*g* to turn OFF the LD 501*d*. That is, the drive current supplied from the drive circuit 501*g* to the LD 501*d* is stopped by the control unit 501*h*. In step S68, supply of platelet measurement specimen is stopped. Thereafter, in step S69, the sheath flow cell 503 is washed.

In the present embodiment, the irradiating intensity is adjusted according to the measurement mode by the selection circuit 501*i* by arranging the selection circuit 501*i* for selecting the irradiating intensity to be irradiated from the LD501*d*, as described above. The irradiating intensity is set to 3.4 mW in the DIFF measurement, the irradiating intensity is set to 10 mW in the PLT measurement, and the accuracy is enhanced in both the DIFF measurement and the PLT measurement.

That is, the blood analyzer 1 of the present embodiment is an analyzer in which the irradiating intensity can be adjusted according to the measurement target. Specifically, the irradiating intensity is made small when measuring large particles such as white blood cells, and the irradiating intensity is made large when measuring small particles such as platelet. The measurement accuracy of small particles then can be enhanced while suppressing the measurement of large particles from becoming difficult.

In the present embodiment, whether or not to perform the DIFF measurement, the RET measurement, and the PLT measurement can be easily accepted by arranging the input device 303 for accepting the measurement mode.

In the present embodiment, the drive current corresponding to the irradiating intensity selected by the selection circuit 501*i* is supplied from the drive circuit 501*g* to the LD 501*d* by the control unit 501*h* by arranging the drive circuit 501*g* for supplying the drive current to the LD 501*d* and the control unit 501*h* for controlling the drive circuit 501*g*, whereby the irradiating intensity can be easily adjusted according to the measurement mode. If irradiation of light from the LD 501*d* is not necessary, the irradiation of the laser light from the LD 501*d* can be stopped, and the lifetime of the LD 501*d* can be extended.

In the present embodiment, the control unit 501*h* is configured to compare the irradiating intensity selected by the selection circuit 501*i* and the irradiating intensity irradiated from the LD 501*d*, and to control the drive circuit 501*g* so that the irradiating intensity irradiated from the LD 501*d* approaches the irradiating intensity selected by the selection circuit 501*i*, so that the irradiating intensity irradiated from the LD 501*d* approaches the irradiating intensity selected by the selection circuit 501*i* when the irradiating intensity irradiated from the LD 501*d* differs from the irradiating intensity selected by the selection circuit 501*i* due to environment temperature etc. Therefore, variation is suppressed from occurring in the irradiating intensity irradiated from the LD 501*d* and the irradiating intensity selected by the selection circuit 501*i*, and thus the measurement accuracy is suppressed from lowering.

In the present embodiment, the drive current supplied from the drive circuit 501*g* to the LD 501*d* is adjusted based on the irradiating intensity irradiated from the LD 501*d* detected by the LD output detection unit 501*i* by arranging the PD 501*e* for receiving the laser light irradiated from the LD 501*d* and converting the same to the electrical signal and the LD output detection unit 501*j* for detecting the irradiating intensity irradiated from the LD 501*d* based on the electrical signal output from the PD 501*e*, and thus the irradiating intensity irradiated from the LD 501*d* can be easily approached to the irradiating intensity selected by the selection circuit 501*i*.

In the present embodiment, the signal to be superimposed on the drive current by the high frequency oscillation circuit 501*f* can be adjusted according to the selected irradiating intensity by the high frequency bias voltage adjustment circuit 501*c* by arranging the high frequency oscillation circuit 501*f* for generating the signal to be superimposed on the drive current supplied to the LD 501*d* and the high frequency bias voltage adjustment circuit 501*c* for adjusting the bias voltage to supply to the high frequency oscillation circuit 501*f* according to the irradiating intensity selected by the selection circuit 501*i*, and thus the light irradiated from the LD 501*d* is in multimode including a great number of oscillation wavelengths regardless of the selected irradiating intensity. The occurrence of mode hopping in which the oscillation mode changes to another mode, which is a problem in the single mode where the light irradiated from the LD 501*d* has a single oscillation wavelength, can be suppressed, and thus the lowering in the measurement accuracy can be suppressed.

The embodiment disclosed herein is merely illustrative in all aspects and should not be recognized as being restrictive. The scope of the invention is defined by the scope of the claims rather than by the description of the embodiment, and meaning equivalent to the claims and all modifications within the scope is encompassed herein.

For instance, a case of applying the present invention to the blood analyzer 1 serving as one example of the analyzer is described in the embodiment, but the present invention is not limited thereto, and may be applied to an analyzer for measuring components in other biological samples such as urine. The analyzer having urine as the biological sample includes a device of measuring, classifying, and counting particle components such as bacteria, red blood cells, white blood cells, casts, and epidermal cells in the urine through the flow cytometry method. The particles in the urine differ in size depending on the type of particles, and thus the intensity of the light to be irradiated on the particles is changed according to the type of particles to be measured.

In the embodiment, a case of arranging the input device 303 having a function of accepting whether or not to perform the DIFF measurement, the RET measurement, and the PLT measurement has been described, but the present invention is not limited thereto, and whether or not to perform the DIFF measurement, the RET measurement, and the PLT measurement may be accepted through an electrical communication line from the server computer etc.

In the embodiment, a case of arranging the selection circuit 501i for selecting the output of the LD 501d by controlling the drive current to be supplied to the LD 501d is described, but the present invention is not limited thereto, and the selection circuit for selecting the output of the LD may be arranged by arranging a predetermined neutral density filter on the path of the laser light.

In the embodiment, a case of configuring the measurement section 2 and the data processing section 3 as separate devices has been described, but the present invention is not limited thereto; and the measurement section and the data processing section may be configured as an integrated device.

In the embodiment, a case of having the output of the LD 501d as 3.4 mW, 6 mW, or 10 mW has been described, but the present invention is not limited thereto, and the output of the LD may be set to other values.

The invention claimed is:

1. An analyzer for analyzing a biological sample, comprising:
   a measurement specimen preparation section configured for preparing a measurement specimen with a reagent and the biological sample;
   an irradiator configured for outputting a light at a variable intensity to irradiate the measurement specimen;
   a first light receiving section configured for receiving a light from the irradiated measurement specimen and converting the received light into an electrical signal;
   a analysis section configured for analyzing the measurement specimen based on the electrical signal outputted by the first light receiving section; and
   a power control section responsive to an intensity selection signal to adjust a drive current to drive the irradiator such that the irradiator outputs the light at an intensity selected by the intensity selection signal.

2. The analyzer according to claim 1, further comprising an accepting section configured for receiving a selection of a measurement mode, wherein the power control section is responsive to an intensity selection signal indicative of the selected measurement mode to adjust the drive current for the irradiator such that the irradiator outputs the light at an intensity specified by the intensity selection signal for the selected measurement mode measurement mode.

3. The analyzer according to claim 1, wherein the power control section comprises:
   a drive circuit configured for supplying a variable drive current to the irradiator such that the irradiator selectively outputs the light at different intensities; and
   a drive circuit control unit responsive to the intensity selection signal to direct the drive circuit to adjust the drive current such that the irradiator outputs the light selected by the intensity selection signal.

4. The analyzer according to claim 3, wherein the drive circuit control unit comprises:
   a detection section configured for detecting the light outputted from the irradiator; and
   an error amplification unit configured for directing the drive circuit to correct the drive current for the irradiator so as to eliminate any difference between the selected intensity and the intensity of the light detected by the detection section.

5. An analyzer for analyzing a biological sample, comprising:
   an irradiator configured for irradiating a measurement specimen with a light having variable intensity;
   a first light receiving section configured for receiving a light from the irradiated measurement specimen and converting the received light into an electrical signal;
   a analysis section configured for analyzing the measurement specimen based on the electrical signal output by the first light receiving section;
   a drive circuit configured for supplying a variable drive current to the irradiator such that the irradiator selectively outputs the light at different intensities;
   a drive circuit control unit responsive to an intensity selection signal to direct the drive circuit to adjust the drive current such that the irradiator outputs the light at an intensity selected by the intensity selection signal;
   an oscillation circuit configured for generating a signal to be superimposed on the drive current supplied to the irradiator; and
   an oscillation circuit control unit configured for controlling the oscillation circuit according to the specified intensity.

6. The analyzer according to claim 5, wherein the oscillation circuit control unit includes a bias voltage adjustment circuit configured for adjusting a bias voltage to be supplied to the oscillation circuit according to the specified intensity.

7. The analyzer according to claim 1, wherein the biological sample includes blood.

8. The analyzer according to claim 7, further comprising an accepting section configured for receiving a selection of a measurement mode selected from among a white blood cell differentiation measurement mode, a reticulocyte measurement mode and a platelet measurement mode, wherein the power control section is responsive to an intensity selection signal indicative of the selected measurement mode to adjust the drive current for the irradiator such that the irradiator outputs the light at an intensity specified by the intensity selection signal for the selected measurement mode.

9. The analyzer according to claim 8, wherein the specified intensities are different respectively for the white blood cell differentiation measurement mode, measurement in the reticulocyte measurement mode, and measurement in the platelet measurement mode.

10. The analyzer according to claim 9, wherein the analysis section comprises:
- a first distribution chart creating part for creating a first distribution chart based on a first electrical signal output from the first light receiving section when the analyzer operates under the white blood cell differentiation measurement mode;
- a second distribution chart creating part for creating a second distribution chart based on a second electrical signal output from the first light receiving section when the analyzer operates under the reticulocyte measurement mode; and
- a third distribution chart creating part for creating a third distribution chart based on a third electrical signal output from the first light receiving section when the analyzer operates under the platelet measurement mode.

11. The analyzer according to claim 1, further comprising a flow cell configured for flowing the measurement specimen therethrough, wherein the irradiator irradiates the light to the measurement specimen flowing through the flow cell.

12. An analyzer for analyzing a biological sample, comprising:
- a measurement specimen preparation section configured for preparing a measurement specimen with a reagent and the biological sample;
- an irradiator configured for outputting a light at a variable intensity to irradiate the measurement specimen;
- a light receiving section configured for receiving a light from the irradiated measurement specimen and converting the received light into an electrical signal;
- an analysis section configured for analyzing the measurement specimen based on the electrical signal output by the light receiving section;
- an accepting section for receiving a selection of a measurement mode; and
- a power control unit responsive to the selection of the measurement mode to adjust a drive current to drive the irradiator such that the irradiator outputs the light at an intensity specified for selected measurement mode.

13. An analyzer for analyzing a biological sample, comprising:
- an accepting section for receiving a selection of a measurement mode;
- a measurement specimen preparation section configured for preparing a measurement specimen, using a reagent and the biological sample, which is prepared for analysis under the selected measurement mode;
- an irradiator configured for outputting a light at a variable intensity to irradiate the measurement specimen, wherein the irradiator is responsive to the selection of the measurement mode to output the light at an intensity specified for the selected measurement mode;
- a photoelectric conversion element configured for photoelectrically converting the light from the irradiated measurement specimen;
- an analysis section configured for analyzing the measurement specimen based on an electrical signal from the photoelectric conversion element in such a manner peculiar to the selected measurement mode.

14. The analyzer according to claim 13, wherein the accepting section receives selections of a first measurement mode and a second measurement mode, and the measurement specimen preparation section prepares a first measurement specimen for the first measurement mode and a second measurement specimen for the second measurement mode using from one biological sample.

15. The analyzer according to claim 14, further comprising a flow cell for flowing the first and second measurement specimens therethrough, wherein
the irradiator outputs the light at a first intensity to irradiates the first measurement specimen flowing through the flow cell under the first measurement mode, and
the irradiator outputs the light at a second intensity to irradiates the second measurement specimen flowing through the flow cell under the second measurement mode.

16. The analyzer according to claim 13, wherein the analyzer counts particles in the biological sample.

17. The analyzer according to claim 16, wherein the biological sample is blood, and the particles are blood cells.

18. The analyzer according to claim 16, wherein the biological sample is urine, and the particles are one of bacteria, red blood cells, white blood cells, casts, and epidermal cells in the urine.

19. The analyzer according to claim 16, wherein particles to be counted in the second measurement mode particles larger than particles to be counted in the first measurement mode, and
under the second measurement mode, the irradiator outputs the light at an intensity lower than an intensity at which the irradiator outputs the light under the first measurement mode.

* * * * *

UNITED STATES PATENT AND TRADEMARK OFFICE
CERTIFICATE OF CORRECTION

| | | |
|---|---|---|
| PATENT NO. | : 7,981,662 B2 | Page 1 of 1 |
| APPLICATION NO. | : 12/079650 | |
| DATED | : July 19, 2011 | |
| INVENTOR(S) | : Kunio Ueno et al. | |

It is certified that error appears in the above-identified patent and that said Letters Patent is hereby corrected as shown below:

<u>In the Claims</u>

In column 13, claim 1, line 57, before "analysis section configured" replace "a" with --an--.

In column 14, claim 2, line 4, delete "measurement mode" (second occurrence).

In column 14, claim 3, line 12, after "outputs the light" insert --at the intensity--.

In column 14, claim 5, line 31, before "analysis section configured" replace "a" with --an--.

In column 15, claim 12, line 39, after "intensity specified for" insert --the--.

In column 16, claim 14, lines 15-16, after "measurement mode, and" start a new paragraph with "the measurement specimen".

In column 16, claim 14, line 19, after "measurement mode" delete "using".

In column 16, claim 15, lines 24-25, after "intensity to" replace "irradiates" with --irradiate--.

In column 16, claim 15, line 28, before "the second measurement" replace "irradiates" with --irradiate--.

In column 16, claim 19, line 40, after "second measurement mode" insert --are--.

Signed and Sealed this
Seventeenth Day of April, 2012

David J. Kappos
*Director of the United States Patent and Trademark Office*